United States Patent
Iwata et al.

(10) Patent No.: US 9,288,985 B2
(45) Date of Patent: Mar. 22, 2016

(54) PLANT DISEASE CONTROL COMPOSITION

(71) Applicant: SUMITOMO CHEMICAL COMPANY, LIMITED, Tokyo (JP)

(72) Inventors: Atsushi Iwata, Tokyo (JP); Makoto Kurahashi, Hyogo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/369,787

(22) PCT Filed: Jan. 21, 2013

(86) PCT No.: PCT/JP2013/051682
§ 371 (c)(1),
(2) Date: Jun. 30, 2014

(87) PCT Pub. No.: WO2013/111893
PCT Pub. Date: Aug. 1, 2013

(65) Prior Publication Data
US 2014/0364478 A1 Dec. 11, 2014

(30) Foreign Application Priority Data
Jan. 24, 2012 (JP) .................................. 2012-011777

(51) Int. Cl.
A01N 37/30 (2006.01)
A01N 43/50 (2006.01)
A01N 43/653 (2006.01)
A01N 43/36 (2006.01)
A01N 37/18 (2006.01)

(52) U.S. Cl.
CPC ............... *A01N 43/36* (2013.01); *A01N 37/18* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,410,316 B2* | 4/2013 | Itoh et al. | ...................... | 568/583 |
| 8,524,637 B2* | 9/2013 | Soma et al. | ................... | 504/139 |
| 8,796,176 B2* | 8/2014 | Takaishi et al. | ............... | 504/100 |
| 8,871,762 B2* | 10/2014 | Kiguchi et al. | ............ | 514/237.5 |
| 8,916,595 B2* | 12/2014 | Kiguchi et al. | ................ | 514/367 |
| 8,940,717 B2* | 1/2015 | Kiguchi et al. | ................ | 514/81 |
| 8,940,777 B2* | 1/2015 | Soma et al. | ................... | 514/365 |
| 8,940,795 B2* | 1/2015 | Kiguchi et al. | ............... | 514/622 |
| 8,946,298 B2* | 2/2015 | Kiguchi et al. | ............... | 514/621 |
| 2004/0254237 A1 | 12/2004 | Nakamura et al. | | |
| 2010/0267565 A1* | 10/2010 | Kurahashi et al. | ............ | 504/322 |
| 2013/0123321 A1 | 5/2013 | Matsuzaki | | |
| 2014/0038823 A1* | 2/2014 | Dahmen et al. | ............... | 504/103 |
| 2014/0171426 A1* | 6/2014 | Iwata et al. | ................ | 514/229.2 |
| 2014/0179692 A1* | 6/2014 | Iwata et al. | ................ | 514/229.2 |
| 2014/0187541 A1* | 7/2014 | Iwata et al. | ................ | 514/229.2 |
| 2014/0200140 A1* | 7/2014 | Ikeda | ............................ | 504/128 |
| 2014/0200248 A1* | 7/2014 | Iwata et al. | ................... | 514/384 |
| 2014/0206730 A1* | 7/2014 | Iwata et al. | ................... | 514/383 |
| 2014/0206731 A1* | 7/2014 | Iwata et al. | ................... | 514/383 |
| 2014/0221363 A1* | 8/2014 | Iwata et al. | ................ | 514/229.2 |
| 2014/0221432 A1* | 8/2014 | Iwata et al. | ................... | 514/341 |
| 2014/0221440 A1* | 8/2014 | Iwata et al. | ................... | 514/383 |
| 2014/0221441 A1* | 8/2014 | Iwata et al. | ................... | 514/384 |
| 2014/0249187 A1* | 9/2014 | Iwata et al. | ................... | 514/341 |
| 2014/0275051 A1* | 9/2014 | Iwata et al. | ................ | 514/229.2 |
| 2014/0275052 A1* | 9/2014 | Iwata et al. | ................ | 514/229.2 |
| 2014/0275053 A1* | 9/2014 | Iwata et al. | ................ | 514/229.2 |
| 2014/0275177 A1* | 9/2014 | Iwata et al. | ................... | 514/341 |
| 2014/0288104 A1* | 9/2014 | Iwata et al. | ................... | 514/269 |
| 2014/0288130 A1* | 9/2014 | Iwata et al. | ................... | 514/341 |
| 2014/0288131 A1* | 9/2014 | Iwata et al. | ................... | 514/341 |
| 2014/0296269 A1* | 10/2014 | Iwata et al. | ................... | 514/269 |
| 2014/0296298 A1* | 10/2014 | Iwata et al. | ................... | 514/341 |
| 2014/0371288 A1* | 12/2014 | Iwata et al. | ................... | 514/419 |
| 2015/0094203 A1* | 4/2015 | Ikeda | ............................ | 504/225 |
| 2015/0099630 A1* | 4/2015 | Ikeda | ............................ | 504/128 |

FOREIGN PATENT DOCUMENTS

| | | |
|---|---|---|
| CN | 1455641 | 11/2003 |
| CN | 101410016 | 4/2009 |
| CN | 102017954 | 4/2011 |
| JP | 07-149701 | 6/1995 |
| JP | 07149701 A * | 6/1995 |
| JP | 11-255607 | 9/1999 |
| JP | 11255607 A * | 9/1999 |
| JP | 2001-139405 | 5/2001 |

(Continued)

OTHER PUBLICATIONS

Extended European Search Report dated Jul. 6, 2015, issued in corresponding European Patent Application No. 13741192.2.

(Continued)

*Primary Examiner* — Nyeemah A Grazier

(74) *Attorney, Agent, or Firm* — Wenderoth, Lind & Ponack, L.L.P.

(57) ABSTRACT

To provide a plant disease control composition having excellent control effect against plant diseases.

A plant disease control composition comprising an amide compound represented by formula (I):

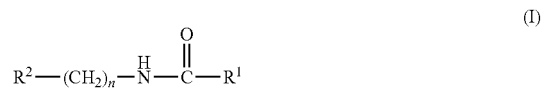

wherein each symbol is as defined in the description, and fludioxonil has excellent control effect against plant diseases.

7 Claims, No Drawings

(56) References Cited

FOREIGN PATENT DOCUMENTS

| | | | |
|---|---|---|---|
| JP | 2001139405 A | * | 5/2001 |
| JP | 2003-176258 | | 6/2003 |
| JP | 2009-501709 | | 1/2009 |
| JP | 2009-132690 | | 6/2009 |
| WO | WO 9945774 A1 | * | 9/1999 |
| WO | 02/21918 | | 3/2002 |
| WO | 2007/006734 | | 1/2007 |
| WO | 2007/090623 | | 8/2007 |
| WO | 2009/057668 | | 5/2009 |
| WO | 2010/137676 | | 12/2010 |
| WO | 2011/124586 | | 10/2011 |
| WO | WO 2012143127 A1 | * | 10/2012 |

OTHER PUBLICATIONS

"Syngenta Seedcare Soybean Portfolio Outshines the Competition TM", Syngenta Seedcare, Jan. 1, 2011, pp. 1-5.

Chastagner et al., "Efficacy of Fungicides in Controlling Leaf Spot on Bulbous Iris", Acta Horticulture, International Society for Horticultural Science, Be, Jan. 1, 2005, vol. 673, pp. 509-512.

Itagaki et al., "Biological activities and structure-activity relationship of substitution compounds of $N$-[2-(3-indolyl)ethyl]succinamic acid and $N$-[2-(1-naphthyl)ethyl]succinamic acid, derived from a new category of root-promoting substances, $N$-(phenethyl)succinamic acid analogs", Plant and Soil, Aug. 1, 2003, vol. 255, No. 1, pp. 67-75.

International Search Report dated Mar. 19, 2013, issued in International (PCT) Application No. PCT/JP2013/051682.

International Preliminary Report of Patentability dated Jul. 29, 2014, issued in International (PCT) Application No. PCT/JP2013/051682.

C.D.S. Tomlin, "The Pesticide Manual", $15^{th}$ Edition (published by BCPC) ISBN 978-1-901396-18-8, pp. 520-521.

Chinese First Office Action and Search Report issued Jun. 18, 2015, in corresponding Chinese Application No. 201380006244.4 (with English translation).

Chilean Office Action dated Oct. 23, 2015, issued in corresponding Chilean Application No. 2014-001944 (with English Translation).

Australian Office Action dated Nov. 27, 2015, issued in corresponding Australian Patent Application No. 2013212888.

* cited by examiner

PLANT DISEASE CONTROL COMPOSITION

TECHNICAL FIELD

The present invention relates to a plant disease control composition, and a method for controlling plant diseases.

BACKGROUND ART

A large number of compounds have hitherto been known as active ingredients of a plant disease control composition (see, for example, The Pesticide Manual—15th edition (published by BCPC) ISBN 978-1-901396-18-8).

DISCLOSURE of INVENTION

Problems to be Solved by the Invention

An object of the present invention is to provide a plant disease control composition having excellent control effect against plant diseases.

Means for Solving the Problems

The present inventors have intensively studied so as to find a plant disease control composition having excellent control effect against plant diseases, and found that a composition comprising an amide compound represented by formula (I) shown below, and fludioxonil has excellent control effect against plant diseases.

That is, the present invention includes the following [1] to [5]:

[1] A plant disease control composition comprising:
an amide compound represented by formula (I):

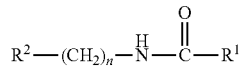

wherein
n represents any integer of from 1 to 4,
$R^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1-C6)alkyl, or (C1-C6 alkoxy)carbonyl(C2-C6)alkenyl, and $R^2$ represents phenyl, 1-naphthyl, or 3-indolyl, provided that, in the substituent represented by $R^2$, any carbon atom which composes phenyl, 1-naphthyl, and 3-indolyl, and also can have a substituent, may each independently have halogen atom, hydroxyl, nitro, C1-C6 alkyl, or C1-C6 alkoxy as a substituent, and fludioxonil;

[2] The plant disease control composition according to [1], wherein a ratio of the content of the amide compound to that of fludioxonil is from 1,000:1 to 1:10 in terms of a weight ratio;

[3] A method for controlling plant diseases, which comprises the step of applying of an effective amount of the plant disease control composition according to according to [1] or [2] to plants or soil in which plants are grown;

[4] A method for controlling plant diseases, which comprises the step of applying an effective amount of the plant disease control composition according to [1] or [2] to plant seeds; and

[5] The method for controlling plant diseases according to [4], wherein the plant seeds are seeds of corn, cotton, soybean, sugar beet, rapeseed, wheat, or rice.

Effects of the Invention

According to the present invention, it is possible to control plant diseases.

Mode for Carrying Out the Invention

The plant disease control composition of the present invention comprises an amide compound (hereinafter referred to as the present amide compound) represented by formula (I):

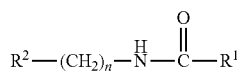

wherein
n represents any integer of from 1 to 4,
$R^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1-C6)alkyl, or (C1-C6 alkoxy)carbonyl(C2-C6)alkenyl, and $R^2$ represents phenyl, 1-naphthyl, or 3-indolyl, provided that, in the substituent represented by $R^2$, any carbon atom which composes phenyl, 1-naphthyl, and 3-indolyl, and also can have a substituent, may each independently have halogen atom, hydroxyl, nitro, C1-C6 alkyl, or C1-C6 alkoxy as a substituent, and fludioxonil.

In formula (I), the (hydroxycarbonyl)C1-C6 alkyl represented by $R^1$ includes, for example, hydroxycarbonylmethyl, 2-(hydroxycarbonyl)ethyl, 3-(hydroxycarbonyl)propyl, and 4-(hydroxycarbonyl)butyl; the (hydroxycarbonyl)C2-C6 alkenyl includes, for example, 2-(hydroxycarbonyl)ethenyl, 3-(hydroxycarbonyl)-2-propenyl, and 3-(hydroxycarbonyl)-1-propenyl; the (aminocarbonyl)C1-C6 alkyl includes, for example, aminocarbonylmethyl, 2-(aminocarbonyl)ethyl, 3-(aminocarbonyl)propyl, and 4-(aminocarbonyl)butyl; the (aminocarbonyl)C2-C6 alkenyl includes, for example, 2-(aminocarbonyl)ethenyl, 3-(aminocarbonyl)-2-propenyl, and 3-(aminocarbonyl)-1-propenyl; the C1-C6 alkoxy)carbonyl(C1-C6)alkyl includes, for example, methoxycarbonylmethyl, 2-(methoxycarbonyl)ethyl, 3-(methoxycarbonyl)propyl, 4-(methoxycarbonyl)butyl, ethoxycarbonylmethyl, 2-(ethoxycarbonyl)ethyl, 3-(ethoxycarbonyl)propy, and 4-(ethoxycarbonyl)butyl; and the (C1-C6 alkoxy)carbonyl (C2-C6)alkenyl includes, for example, 2-(methoxycarbonyl)ethenyl, 3-(methoxycarbonyl)-2-propenyl, 3-(methoxycarbonyl)-1-propenyl, 2-(ethoxycarbonyl)ethenyl, 3-(ethoxycarbonyl)-2-propenyl, and 3-(ethoxycarbonyl)-1-propenyl.

Among substituents represented by $R^2$ of formula (I), each of which may be independently included in any carbon atom which composes phenyl, 1-naphthyl, and 3-indolyl, and also can have a substituent,
the halogen atom includes, for example, fluorine atom, chlorine atom, bromine atom, and iodine atom;
the C1-C6 alkyl includes, for example, methyl, ethyl, propyl, butyl, pentyl, hexyl, 1-methylethyl, 2-methylpropyl, 3-methylbutyl, and 4-methylpentyl; and
the C1-C6 alkoxy includes, for example, methoxy, ethoxy, propoxy, butoxy, pentyloxy, hexyloxy, 1-methylethoxy, 2-methylpropoxy, 3-methylbutoxy, and 4-methylpentyloxy.

In the substituent represented by R² of formula (I), two or more carbon atoms which compose phenyl, 1-naphthyl, and 3-indolyl, and also can have a substituent, sometimes have halogen atom, hydroxyl, nitro, C1-C6 alkyl, or C1-C6 alkoxy as a substituent, simultaneously. In such case, the substituents included in the respective carbon atoms may be the same or different from each other.

The aspect of the present amide compound includes, for example, the followings:

an amide compound in which R¹ is (hydroxycarbonyl)C1-C6 alkyl or (C1-C6 alkoxycarbonyl)C1-C6 alkyl, and R² is phenyl in formula (I);

an amide compound in which n is 2, R¹ is (hydroxycarbonyl)C1-C6 alkyl or (C1-C6 alkoxycarbonyl)C1-C6 alkyl, and R² is phenyl in formula (I); and an amide compound in which R¹ is (hydroxycarbonyl)C1-C3 alkyl or (C1-C2 alkoxy)carbonyl(C1-C3)alkyl, and R² is phenyl, 1-naphthyl, 3-indolyl, or 5-methyl-3-indolyl in formula (I).

The present amide compound sometimes exists in the form of a pesticidally acceptable salt depending on the existential state.

Specific examples of the present amide compound will be shown below.

Amide compounds represented by formula (I-a):

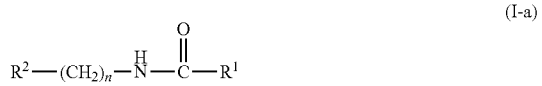

(I-a)

wherein a combination of n, R¹, and R² represents any one of combinations shown in Table 1.

TABLE 1

| Compound No. | n | R¹ | R² |
|---|---|---|---|
| 1 | 1 | hydroxycarbonylmethyl | 1-naphthyl |
| 2 | 1 | methoxycarbonylmethyl | 1-naphthyl |
| 3 | 1 | 2-(hydroxycarbonyl)ethyl | 1-naphthyl |
| 4 | 1 | 2-(hydroxycarbonyl)ethyl | phenyl |
| 5 | 1 | 3-(hydroxycarbonyl)propyl | 1-naphthyl |
| 6 | 1 | 3-(methoxycarbonyl)propyl | 1-naphthyl |
| 7 | 1 | 3-(ethoxycarbonyl)propyl | 1-naphthyl |
| 8 | 1 | 3-(propoxycarbonyl)propyl | 1-naphthyl |
| 9 | 1 | 3-(aminocarbonyl)propyl | 1-naphthyl |
| 10 | 1 | 2-(hydroxycarbonyl)ethenyl | 1-naphthyl |
| 11 | 3 | 2-(hydroxycarbonyl)ethyl | phenyl |
| 12 | 3 | 2-(methoxycarbonyl)ethyl | phenyl |
| 13 | 4 | 2-(hydroxycarbonyl)ethyl | phenyl |
| 14 | 4 | 2-(methoxycarbonyl)ethyl | phenyl |
| 15 | 3 | 3-(hydroxymethyl)propyl | phenyl |
| 16 | 3 | 3-(methoxycarbonyl)propyl | phenyl |
| 17 | 2 | 3-(hydroxycarbonyl)propyl | phenyl |
| 18 | 2 | 3-(methoxycarbonyl)propyl | phenyl |
| 19 | 2 | 3-(hydroxycarbonyl)propyl | 3-indolyl |
| 20 | 2 | 3-(methoxycarbonyl)propyl | 3-indolyl |
| 21 | 2 | 3-(ethoxycarbonyl)propyl | 3-indolyl |
| 22 | 2 | 3-(propoxycarbonyl)propyl | 3-indolyl |
| 23 | 2 | 3-(hydroxycarbonyl)propyl | 5-methyl-3-indolyl |
| 24 | 2 | 3-(hydroxycarbonyl)propyl | 1-naphthyl |
| 25 | 2 | 3-(methoxycarbonyl)propyl | 1-naphthyl |
| 26 | 2 | 3-(ethoxycarbonyl)propyl | 1-naphthyl |
| 27 | 2 | 3-(hydroxycarbonyl)butyl | phenyl |
| 28 | 2 | 3-(methoxycarbonyl)butyl | phenyl |
| 29 | 2 | 2-(methoxycarbonyl)ethyl | phenyl |
| 30 | 2 | 2-(ethoxycarbonyl)ethyl | phenyl |
| 31 | 2 | 2-(propoxycarbonyl)ethyl | phenyl |
| 32 | 2 | 2-(2-methylethoxycarbonyl)ethyl | phenyl |
| 33 | 2 | 2-(methoxycarbonyl)ethyl | 4-fluorophenyl |

TABLE 1-continued

| Compound No. | n | R¹ | R² |
|---|---|---|---|
| 34 | 2 | 2-(methoxycarbonyl)ethyl | 4-chlorophenyl |
| 35 | 2 | 2-(methoxycarbonyl)ethyl | 4-bromophenyl |
| 36 | 2 | 2-(methoxycarbonyl)ethyl | 4-iodophenyl |
| 37 | 2 | 2-(methoxycarbonyl)ethyl | 2-chlorophenyl |
| 38 | 2 | 2-(methoxycarbonyl)ethyl | 3-chlorophenyl |
| 39 | 2 | 2-(methoxycarbonyl)ethyl | 3,4-dichlorophenyl |
| 40 | 2 | 2-(hydroxycarbonyl)ethyl | 4-methylphenyl |
| 41 | 2 | 2-(hydroxycarbonyl)ethyl | 4-methoxyphenyl |
| 42 | 2 | 2-(hydroxycarbonyl)ethyl | 4-fluorophenyl |
| 43 | 2 | 2-(hydroxycarbonyl)ethyl | 4-chlorophenyl |
| 44 | 2 | 2-(hydroxycarbonyl)ethyl | 4-bromophenyl |
| 45 | 2 | 2-(hydroxycarbonyl)ethyl | 4-iodophenyl |
| 46 | 2 | 2-(hydroxycarbonyl)ethyl | 4-nitrophenyl |
| 47 | 2 | 2-(hydroxycarbonyl)ethyl | 2-chlorophenyl |
| 48 | 2 | 2-(hydroxycarbonyl)ethyl | 3,4-dichlorophenyl |
| 49 | 2 | 2-(hydroxycarbonyl)ethyl | phenyl |
| 50 | 2 | 4-(methoxycarbonyl)butyl | phenyl |
| 51 | 2 | 4-(hydroxycarbonyl)butyl | phenyl |

The present amide compound is a compound disclosed, for example, in Japanese Unexamined Patent Publication (Kokai) No. 11-255607 and Japanese Unexamined Patent Publication (Kokai) No. 2001-139405, and can be synthesized, for example, by the methods disclosed in the publications.

Fludioxonil used in the present invention is a known compound and is disclosed, for example, in "The Pesticide Manual-15th edition (published by BCPC); ISBN 978-1-901396-18-8" on page 520. These compounds are obtained from commercially available formulations, or they can be produced by a known method.

In the plant disease control composition of the present invention, the weight ratio of the present amide compound to fludioxonil is not particularly limited, and the amount of fludioxonil is usually from 1 to 10,000 parts by weight, and preferably from 10 to 1,000 parts by weight, based on 1,000 parts by weight of the present amide compound.

The plant disease control composition of the present invention may be a mixture per se of the present amide compound and fludioxonil, and is usually obtained by mixing the present amide compound with fludioxonil and an inert carrier, optionally adding a surfactant and other auxiliaries for formulation, and then formulating the mixture into an oil solution, an emulsifiable concentrate, a flowable formulation, a wettable powder, a water dispersible granule, a dust, or a granule.

The thus formulated plant disease control composition can be used directly as a plant disease control agent, or used after the addition of other inert ingredients.

The total amount of the present amide compound and fludioxonil in the plant disease control composition of the present invention is usually within a range from 0.1% to 100% by weight, preferably from 0.2 to 90% by weight, and more preferably from 1 to 80% by weight.

Examples of the inert carrier used in the case of formulation include a solid carrier and a liquid carrier. Examples of the solid carrier include fine powders or granules of minerals such as kaolin clay, attapulgite clay, bentonite, montmorillonite, acidic white clay, pyrophylite, talc, diatomaceous earth, and calcite; natural organic substances such as corncob flour and walnut shell flour; synthetic organic substances such as urea; salts such as calcium carbonate and ammonium sulfate; and synthetic inorganic substances such as synthetic hydrated silicon oxide. Examples of the liquid carrier include aromatic hydrocarbons such as xylene, alkylbenzene, and methylnaphthalene; alcohols such as 2-propanol, ethylene glycol, propylene glycol, and ethylene glycol monoethyl ether; ketones such as acetone, cyclohexanone, and isophorone; vegetable oils such as soybean oil and cottonseed oil; and petroleum-based aliphatic hydrocarbons, esters, dimethyl sulfoxide, acetonitrile, and water.

Examples of the surfactant include anionic surfactants such as alkyl sulfate ester salts, alkylaryl sulfonates, dialkyl sulfosuccinates, polyoxyethylenealkylaryl ether phosphate ester salts, lignin sulfonates, and naphthalene sulfonate formaldehyde polycondensates; nonionic surfactants such as polyoxyethylene alkylaryl ethers, polyoxyethylene alkylpolyoxypropylene block copolymers, and sorbitan fatty acid esters; and cationic surfactants such as alkyltrimethylammonium salts.

Examples of the other auxiliary for formulation include water-soluble polymers such as polyvinyl alcohol and polyvinyl pyrrolidone; polysaccharides such as gum arabic, alginic acid and a salt thereof, carboxymethyl cellulose (CMC), and xanthane gum; inorganic substances such as aluminum magnesium silicate and alumina sol; preservatives; colorants; and stabilizers such as isopropyl acid phosphate (PAP).

The plant disease control composition of the present invention can control plant diseases by applying to plants or soil in which plants are grown.

Examples of plant diseases, which can be controlled by the present invention, include the followings:

Diseases of rice: Helminthosporium leaf spot (*Cochliobolus miyabeanus*), sheath blight (*Rhizoctonia solani*) and Bakanae disease (*Gibberella fujikuroi*);

Diseases of wheat: Fusarium head blight (*Fusarium graminearum, F. avenacerum, F. culmorum, Microdochium nivale*), bunt (*Tilletia caries*), leaf blotch (*Mycosphaerella graminicola*), and glume blotch (*Leptosphaeria nodorum*);

Diseases of corn: smut (*Ustilago maydis*) and brown spot (*Cochliobolus heterostrophus*);

Diseases of citrus: penicillium rot (*Penicillium digitatum, P. italicum*);

Diseases of apple: blossom blight (*Monilinia mali*), and Alternaria leaf spot (*Alternaria alternata* apple pathotype);

Diseases of grape: ripe rot (*Glomerella cingulata*), and gray mold (*Botrytis cinerea*);

Diseases of gourd: Target leaf spot (*Corynespora cassiicola*), gummy stem blight (*Mycosphaerella melonis*), and Fusarium wilt (*Fusarium oxysporum*);

Diseases of rapeseed: sclerotinia rot (*Sclerotinia sclerotiorum*);

Diseases of soybean: purple seed stain (*Cercospora kikuchii*);

Diseases of azuki bean: gray mold (*Botrytis cinerea*) and Sclerotinia rot (*Sclerotinia sclerotiorum*);

Diseases of peanut: leaf spot (*Cercospora personata*), brown leaf spot (*Cercospora arachidicola*), and southern blight (*Sclerotium rolfsii*);

Diseases of cotton: Fusarium wilt (*Fusarium oxysporum*);

Diseases of sugar beat: Cercospora leaf spot (*Cercospora beticola*), and leaf blight (*Thanatephorus cucumeris*);

Diseases of various plants: gray mold (*Botrytis cinerea*), Sclerotinia rot (*Sclerotinia sclerotiorum*), and Damping-off (*Rhizoctonia solani*) caused by *Rhizoctonia* spp.;

Diseases of turfgrass: dollar spot (*Sclerotinia homeocarpa*), brown patch, and large patch (*Rhizoctonia solani*);

Disease of banana: sigatoka (*Mycosphaerella fijiensis, Mycosphaerella musicola, Pseudocercospora musae*); and Seed diseases or diseases in the early stages of the growth of various plants caused by bacteria of *Aspergillus* genus, *Penicillium* genus, *Fusarium* genus, *Thielaviopsis* genus, *Rhizopus* genus, *Mucor* genus, and *Diplodia* genus.

The plant disease control composition of the present invention is applied to crop lands such as cultivated lands, paddy fields, lawns, and orchards, or non-crop lands. The plant disease control composition of the present invention can control plant diseases in crop lands in which "plants" are grown.

Examples of plants, to which the plant disease control composition of the present invention can be applied, include the followings:

Crops: corn, rice, wheat, barley, rye, oat, sorghum, cotton, soybean, adzuki bean, peanut, buckwheat, sugar beet, rapeseed, sunflower, sugar cane, and tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, rapeseed, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, etc.;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date palm, coconut, oil palm, etc.;

Trees other than fruit trees: tea, mulberry, flowering trees (azalea, camellia, hydrangea, sasanqua, Japanese star anise, cherry, tulip tree, crape myrtle, orange osmanthus, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse chestnut, etc.), coral tree, podocarpus, cedar, Japanese cypress, croton, *Euonymus japonicus, Photinia glabra*, etc.;

Lawns: Zoysia (zoysiagrass, Zoysia matrella, etc.), Bermuda grasses (Cynodon dactylon, etc.), bent grasses (Agrostis alba, creeping bent grass, hiland bent, etc.), bluegrasses (meadow grass, bird grass, etc.), fescue (tall fescue, chewings fescue, creeping red fescue, etc.), ryegrasses (darnel, rye grass, etc.), orchard grass, timothy grass, etc.; and Others: flowers (rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia, etc.), bio-fuel plants (Jatropha, safflower, camelina, switchgrass, Miscanthus, reed canary grass, giant reed, kenaf, cassava, willow, etc.), ornamental plants, etc.

The above "plants" may be those having resistance, which are imparted by a genetic engineering technique or a cross-breeding method.

The plant disease control composition of the present invention can control plant diseases by applying to plants or area in which plants are grown. Examples of the plant as used herein include stems and leaves of the plant, flowers of the plant, fruits of the plant, seeds of the plant, and bulbs of the plant. The bulbs as used herein mean scaly bulbs, corms, root stalks, tubers, tuberous roots, and rhizophores.

The method for controlling plant diseases of the present invention includes application of the plant disease control composition of the present invention to plants, and specific examples thereof include application to the stems and leaves of plants, such as foliage application; application to seeds of plants; and application to area in which plants are grown such as soil application.

Specific examples of the method of application to the stems and leaves of plants, such as foliage application include a method of applying to surfaces of plants which are grown, by ground application which is conducted using a hand sprayer, a power sprayer, a boom sprayer, or a PANCRU-sprayer; or aerial application which is conducted using aerial control or an unmanned helicopter.

The treatment of seeds of plants in the present invention is, for example, a treatment of seeds or bulbs of plants with the plant disease control composition of the present invention. Specific examples thereof include spraying treatment of spraying over surfaces of seeds or bulbs, spray coating treatment of spray coating seeds or bulbs, immersion treatment, film coating treatment, and pellet coating treatment.

Specific examples of the application to area in which plants are grown, such as soil treatment or submerged application in the present invention include planting hole application, plant foot application, in-furrow application, overall application, side ditch application, nursery box application, nursery bed application, and nursery soil incorporation.

When the plant disease control composition of the present invention is applied to plants or area in which plants are grown, the application amount varies depending on the kinds of plants, the kinds or population size of plant diseases to be controlled, the form of a formulation, the timing of application, and weather conditions. The application amount is usually from 0.05 to 10,000 g, and preferably from 0.5 to 1,000 g, per 1,000 m$^2$ of an area in which plants are grown, in terms of the total amount of the present amide compound and fludioxonil.

When seeds of plants are treated with the plant disease control composition of the present invention, the amount varies depending on the kinds of plants, the kinds or population size of plant diseases to be controlled, the form of a formulation, the timing of application, and weather conditions. The amount is usually from 0.001 to 100 g, and preferably from 0.05 to 50 g, per 1 kg of seeds, in terms of the total amount of the present amide compound and fludioxonil.

The plant disease control composition of the present invention in the form of an emulsifiable concentrate, a wettable powder, and a flowable formulation is usually applied by spraying after dilution with water. In this case, the total concentration of the present amide compound and fludioxonil is usually within a range from 0.00001 to 10% by weight, and preferably from 0.0001 to 5% by weight.

A dust and a granule are usually applied as they are without dilution.

EXAMPLES

The present invention will be described in more detail by way of Formulation Examples and Test Examples, but the present invention is not limited only thereto. In the Examples, parts are by weight unless otherwise specified. In the Examples, compounds specified by the description of the "present amide compound (compound No. 4)" are the same as those specified by "compound No." corresponding to the description of Table 1.

First, Formulation Examples will be shown.

Formulation Example 1

Ten (10) parts the present amide compound (compound No. 5), 1 part of fludioxonil, 35 parts of a mixture (in a weight ratio of 1:1) of white carbon, polyoxyethylene alkyl ether sulfate ammonium salt, and water are mixed to a total amount of 100 parts, and then the mixture is finely ground by a wet grinding method to obtain a formulation.

Formulation Example 2

The same procedure as in Formulation Example 1 is conducted, except that the present amide compound (compound No. 13) is used in place of the present amide compound (compound No. 5), to obtain a formulation.

Formulation Example 3

The same procedure as in Formulation Example 1 is conducted, except that the present amide compound (compound No. 14) is used in place of the present amide compound (compound No. 5), to obtain a formulation.

Formulation Example 4

The same procedure as in Formulation Example 1 is conducted, except that the present amide compound (compound No. 19) is used in place of the present amide compound (compound No. 5), to obtain a formulation.

Formulation Example 5

The same procedure as in Formulation Example 1 is conducted, except that the present amide compound (compound No. 29) is used in place of the present amide compound (compound No. 5), to obtain a formulation.

Formulation Example 6

The same procedure as in Formulation Example 1 is conducted, except that the present amide compound (compound No. 36) is used in place of the present amide compound (compound No. 5), to obtain a formulation.

Formulation Example 7

The same procedure as in Formulation Example 1 is conducted, except that the present amide compound (compound No. 42) is used in place of the present amide compound (compound No. 5), to obtain a formulation.

Formulation Example 8

The same procedure as in Formulation Example 1 is conducted, except that the present amide compound (compound No. 49) is used in place of the present amide compound (compound No. 5), to obtain a formulation.

Formulation Example 9

Ten (10) parts the present amide compound (compound No. 5), 1 part of fludioxonil, 1.5 parts of sorbitan trioleate, and 28 parts of an aqueous solution containing 2 parts of polyvinyl alcohol are mixed, and then the mixture is finely ground by a wet grinding method. An aqueous solution containing 0.05 part of xanthane gum and 0.1 part of magnesium aluminum silicate is added in this mixture to a total amount of 90 parts, and 10 parts of propylene glycol is added, followed by mixing with stirring to obtain a formulation.

Formulation Example 10

The same procedure as in Formulation Example 9 is conducted, except that the present amide compound (compound No. 13) is used in place of the present amide compound (compound No. 5), to obtain a formulation.

Formulation Example 11

The same procedure as in Formulation Example 9 is conducted, except that the present amide compound (compound No. 14) is used in place of the present amide compound (compound No. 5), to obtain a formulation.

Formulation Example 12

The same procedure as in Formulation Example 9 is conducted, except that the present amide compound (compound No. 19) is used in place of the present amide compound (compound No. 5), to obtain a formulation.

Formulation Example 13

The same procedure as in Formulation Example 9 is conducted, except that the present amide compound (compound No. 29) is used in place of the present amide compound (compound No. 5), to obtain a formulation.

Formulation Example 14

The same procedure as in Formulation Example 9 is conducted, except that the present amide compound (compound No. 36) is used in place of the present amide compound (compound No. 5), to obtain a formulation.

Formulation Example 15

The same procedure as in Formulation Example 9 is conducted, except that the present amide compound (compound No. 42) is used in place of the present amide compound (compound No. 5), to obtain a formulation.

Formulation Example 16

The same procedure as in Formulation Example 9 is conducted, except that the present amide compound (compound No. 49) is used in place of the present amide compound (compound No. 5), to obtain a formulation.

Formulation Example 17

Ten (10) parts of the present amide compound (compound No. 5), 2 parts of fludioxonil, 3 parts of calcium lignin sulfonate, 2 parts of sodium lauryl sulfate, and synthetic hydrated silicon oxide as balance are well ground and mixed to obtain 100 parts of a formulation.

Formulation Example 18

The same procedure as in Formulation Example 17 is conducted, except that the present amide compound (compound No. 13) is used in place of the present amide compound (compound No. 5), to obtain a formulation.

Formulation Example 19

The same procedure as in Formulation Example 17 is conducted, except that the present amide compound (compound No. 14) is used in place of the present amide compound (compound No. 5), to obtain a formulation.

Formulation Example 20

The same procedure as in Formulation Example 17 is conducted, except that the present amide compound (compound No. 19) is used in place of the present amide compound (compound No. 5), to obtain a formulation.

Formulation Example 21

The same procedure as in Formulation Example 17 is conducted, except that the present amide compound (compound No. 29) is used in place of the present amide compound (compound No. 5), to obtain a formulation.

Formulation Example 22

The same procedure as in Formulation Example 17 is conducted, except that the present amide compound (compound No. 36) is used in place of the present amide compound (compound No. 5), to obtain a formulation.

Formulation Example 23

The same procedure as in Formulation Example 17 is conducted, except that the present amide compound (compound No. 42) is used in place of the present amide compound (compound No. 5), to obtain a formulation.

Formulation Example 24

The same procedure as in Formulation Example 17 is conducted, except that the present amide compound (compound No. 49) is used in place of the present amide compound (compound No. 5), to obtain a formulation.

Treatment Example 1

The formulation prepared in Formulation Example 1 is subjected to a spray coating treatment in an amount of 500 ml per 100 kg of dried sorghum seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

Treatment Example 2

The formulation prepared in Formulation Example 1 is subjected to a spray coating treatment in an amount of 40 ml per 10 kg of dried corn seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

Treatment Example 3

The formulation prepared in Formulation Example 17 is subjected to a powder coating treatment in an amount of 50 g per 10 kg of dried corn seeds to obtain treated seeds.

The same procedure as mentioned above is conducted, except that the respective formulations prepared in Formulation Examples 18 to 24 are used in place of the formulation prepared in Formulation Example 17, to obtain the respective treated seeds.

Treatment Example 4

The formulation prepared in Formulation Example 1 is subjected to a spray coating treatment in an amount of 50 ml per 10 kg of dried soybean seeds using a rotary seed treatment machine (seed dresser, manufactured by Hans-Ulrich Hege GmbH) to obtain treated seeds.

The same procedure as mentioned above is conducted, except that the respective formulations prepared in Formulation Examples 2 to 16 are used in place of the formulation prepared in Formulation Example 1, to obtain the respective treated seeds.

The effects of the present invention will be illustrated below by way of Test Examples.

Test Example 1

Each of the present amide compounds and fludioxonil was dissolved in dimethyl sulfoxide (DMSO) so as to obtain the concentration that is 150 times the test concentration, and a DMSO solution of each of the present amide compounds and a DMSO solution of fludioxonil were respectively dispensed into each well of a titer plate (with 96 wells) in the amount of 1 µl. Then, 148 µl of a suspension of a potato dextrose liquid medium containing sporidia of smut of corn (*Ustilago maydis*) suspended in advance therein, so as to obtain the concentration of $5 \times 10^4$ sporidia/ml, was added. The plate thus obtained was used as a plate in a treated area.

In contrast, 2 µl of DMSO was dispensed into each well of a titer plate (with 96 wells), and then 148 µl of a suspension of a potato dextrose liquid medium containing sporidia of smut of corn suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing smut of corn to undergo proliferation, and then the absorbance at 550 nm of each well of the titer plate was measured. The value obtained by subtracting the absorbance of the well, into which 150 µl of only a potato dextrose liquid medium has been dispensed, from this value was regarded as the degree of growth of smut of corn.

Based on the calculated degree of growth in a treated area and the calculated degree of growth in non-treated area, bactericidal effect was calculated using Equation 1.

Bactericidal effect = $100 \times (A-B)/A$    "Equation 1"

where
A: Degree of bacterial growth in non-treated area
B: Degree of bacterial growth in treated area

TABLE 2

| Test compounds | Test concentration (ppm) | Bactericidal effect |
| --- | --- | --- |
| Present amide compound (compound No. 5) + Fludioxonil | 2.5 + 0.031 | 90 |
| Present amide compound (compound No. 5) + Fludioxonil | 0.63 + 0.063 | 99 |
| Present amide compound (compound No. 13) + Fludioxonil | 2.5 + 0.031 | 90 |
| Present amide compound (compound No. 13) + Fludioxonil | 0.63 + 0.063 | 99 |
| Present amide compound (compound No. 14) + Fludioxonil | 2.5 + 0.031 | 88 |
| Present amide compound (compound No. 14) + Fludioxonil | 0.63 + 0.063 | 99 |
| Present amide compound (compound No. 19) + Fludioxonil | 2.5 + 0.031 | 87 |
| Present amide compound (compound No. 19) + Fludioxonil | 0.63 + 0.063 | 99 |
| Present amide compound (compound No. 29) + Fludioxonil | 2.5 + 0.031 | 84 |
| Present amide compound (compound No. 29) + Fludioxonil | 0.63 + 0.063 | 100 |
| Present amide compound (compound No. 36) + Fludioxonil | 2.5 + 0.031 | 84 |
| Present amide compound (compound No. 36) + Fludioxonil | 0.63 + 0.063 | 99 |
| Present amide compound (compound No. 49) + Fludioxonil | 2.5 + 0.031 | 84 |
| Present amide compound (compound No. 49) + Fludioxonil | 0.63 + 0.063 | 99 |
| Present amide compound (compound No. 4) + Fludioxonil | 1.3 + 0.013 | 58 |
| Present amide compound (compound No. 4) + Fludioxonil | 2.5 + 0.013 | 69 |
| Present amide compound (compound No. 11) + Fludioxonil | 1.3 + 0.013 | 58 |
| Present amide compound (compound No. 11) + Fludioxonil | 1.3 + 0.025 | 97 |
| Present amide compound (compound No. 13) + Fludioxonil | 1.3 + 0.013 | 53 |
| Present amide compound (compound No. 14) + Fludioxonil | 5 + 0.013 | 57 |
| Present amide compound (compound No. 31) + Fludioxonil | 1.3 + 0.013 | 54 |
| Present amide compound (compound No. 32) + Fludioxonil | 1.3 + 0.013 | 55 |
| Present amide compound (compound No. 32) + Fludioxonil | 1.3 + 0.025 | 95 |
| Present amide compound (compound No. 32) + Fludioxonil | 2.5 + 0.013 | 62 |
| Present amide compound (compound No. 40) + Fludioxonil | 1.3 + 0.013 | 57 |
| Present amide compound (compound No. 40) + Fludioxonil | 1.3 + 0.025 | 95 |
| Present amide compound (compound No. 40) + Fludioxonil | 5 + 0.013 | 75 |
| Present amide compound (compound No. 40) + Fludioxonil | 5 + 0.025 | 98 |
| Present amide compound (compound No. 43) + Fludioxonil | 1.3 + 0.013 | 60 |

Test Example 2

Each of the present amide compounds and fludioxonil was dissolved in dimethyl sulfoxide (DMSO) so as to obtain the concentration that is 150 times the test concentration, and a DMSO solution of each of the present amide compounds and a DMSO solution of fludioxonil were respectively dispensed into each well of a titer plate (with 96 wells) in the amount of 1 µl. Then, 148 µl of a suspension of a potato dextrose liquid medium containing conidia of leaf blotch of wheat (*Mycosphaerella graminicola*) suspended in advance therein, so as to obtain the concentration of $1 \times 10^5$ conidia/ml, was added. The plate thus obtained was used as a plate in a treated area.

In contrast, 2 µl of DMSO was dispensed into each well of a titer plate (with 96 wells), and then 148 µl of a suspension of a potato dextrose liquid medium containing conidia of leaf blotch of wheat suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing leaf blotch of wheat to undergo proliferation, and then the absorbance at 550 nm of each well of the titer plate was measured. The value obtained by subtracting the absorbance of the well, into which 150 μl of only a potato dextrose liquid medium has been dispensed, from this value was regarded as the degree of growth of leaf blotch of wheat. Based on the calculated degree of growth in a treated area and the calculated degree of growth in non-treated area, bactericidal effect was calculated using Equation 1.

TABLE 3

| Test compounds | Test concentration (ppm) | Bactericidal effect |
| --- | --- | --- |
| Present amide compound (compound No. 5) + Fludioxonil | 5.0 + 1.0 | 93 |
| Present amide compound (compound No. 5) + Fludioxonil | 0.63 + 1.0 | 94 |
| Present amide compound (compound No. 13) + Fludioxonil | 5.0 + 1.0 | 91 |
| Present amide compound (compound No. 13) + Fludioxonil | 0.63 + 1.0 | 92 |
| Present amide compound (compound No. 14) + Fludioxonil | 5.0 + 1.0 | 94 |
| Present amide compound (compound No. 14) + Fludioxonil | 0.63 + 1.0 | 95 |
| Present amide compound (compound No. 19) + Fludioxonil | 5.0 + 1.0 | 92 |
| Present amide compound (compound No. 19) + Fludioxonil | 0.63 + 1.0 | 93 |
| Present amide compound (compound No. 29) + Fludioxonil | 5.0 + 1.0 | 94 |
| Present amide compound (compound No. 29) + Fludioxonil | 0.63 + 1.0 | 92 |
| Present amide compound (compound No. 36) + Fludioxonil | 5.0 + 1.0 | 93 |
| Present amide compound (compound No. 36) + Fludioxonil | 0.63 + 1.0 | 94 |
| Present amide compound (compound No. 49) + Fludioxonil | 5.0 + 1.0 | 94 |
| Present amide compound (compound No. 49) + Fludioxonil | 0.63 + 1.0 | 94 |
| Present amide compound (compound No. 4) + Fludioxonil | 1.3 + 0.25 | 52 |
| Present amide compound (compound No. 4) + Fludioxonil | 5.0 + 0.25 | 63 |
| Present amide compound (compound No. 11) + Fludioxonil | 1.3 + 0.25 | 53 |
| Present amide compound (compound No. 11) + Fludioxonil | 1.3 + 0.5 | 92 |
| Present amide compound (compound No. 13) + Fludioxonil | 1.3 + 0.25 | 50 |
| Present amide compound (compound No. 13) + Fludioxonil | 5.0 + 0.5 | 91 |
| Present amide compound (compound No. 14) + Fludioxonil | 2.5 + 0.5 | 93 |
| Present amide compound (compound No. 19) + Fludioxonil | 5.0 + 0.25 | 55 |
| Present amide compound (compound No. 19) + Fludioxonil | 1.3 + 0.25 | 52 |
| Present amide compound (compound No. 31) + Fludioxonil | 5.0 + 0.25 | 53 |
| Present amide compound (compound No. 32) + Fludioxonil | 1.3 + 0.25 | 53 |
| Present amide compound (compound No. 40) + Fludioxonil | 2.5 + 0.25 | 66 |
| Present amide compound (compound No. 40) + Fludioxonil | 1.3 + 0.25 | 49 |
| Present amide compound (compound No. 43) + Fludioxonil | 5.0 + 0.25 | 56 |
| Present amide compound (compound No. 50) + Fludioxonil | 1.3 + 0.5 | 92 |

Test Example 3

Each of the present amide compounds and fludioxonil was dissolved in dimethyl sulfoxide (DMSO) so as to obtain the concentration that is 150 times the test concentration, and a DMSO solution of each of the present amide compounds and a DMSO solution of fludioxonil were respectively dispensed into each well of a titer plate (with 96 wells) in the amount of 1 μl. Then, 148 μl of a suspension of a potato dextrose liquid medium containing conidia of Fusarium head blight of wheat (*Fusarium graminearum*) in advance therein, so as to obtain the concentration of $5 \times 10^3$ conidia/ml, was added. The plate thus obtained was used as a plate in a treated area.

In contrast, 2 μl of DMSO was dispensed into each well of a titer plate (with 96 wells), and then 148 μl of a suspension of a potato dextrose liquid medium containing conidia of Fusarium head blight of wheat suspended in advance therein, so as to obtain the concentration of $5 \times 10^4$ sporidia/ml, was added in the same manner as in the case of the treated area. The plate thus obtained was used as a plate in a non-treated area.

Each of the plate in a treated area and the plate in a non-treated area was cultured at 18° C. for 5 days, thereby allowing foot rot of wheat to undergo proliferation, and then the absorbance at 550 nm of each well of the titer plate was measured. The value obtained by subtracting the absorbance of the well, into which 150 μl of only a potato dextrose liquid medium has been dispensed, from this value was regarded as the degree of growth of *Fusarium* head blight of wheat. Based on the calculated degree of growth in a treated area and the calculated degree of growth in non-treated area, bactericidal effect was calculated using Equation 1.

TABLE 4

| Test compounds | Test concentration (ppm) | Bactericidal effect |
| --- | --- | --- |
| Present amide compound (compound No. 5) + Fludiodxonil | 2.5 + 0.031 | 91 |
| Present amide compound (compound No. 5) + Fludioxonil | 0.63 + 0.063 | 100 |
| Present amide compound (compound No. 13) + Fludioxonil | 2.5 + 0.031 | 90 |
| Present amide compound (compound No. 13) + Fludioxonil | 0.63 + 0.063 | 100 |
| Present amide compound (compound No. 14) + Fludioxonil | 2.5 + 0.031 | 86 |
| Present amide compound (compound No. 14) + Fludioxonil | 0.63 + 0.063 | 100 |
| Present amide compound (compound No. 19) + Fludioxonil | 2.5 + 0.031 | 96 |
| Present amide compound (compound No. 19) + Fludioxonil | 0.63 + 0.063 | 100 |
| Present amide compound (compound No. 29) + Fludioxonil | 2.5 + 0.031 | 94 |
| Present amide compound (compound No. 29) + Fludioxonil | 0.63 + 0.063 | 100 |

TABLE 4-continued

| Test compounds | Test concentration (ppm) | Bactericidal effect |
|---|---|---|
| Present amide compound (compound No. 36) + Fludioxonil | 0.63 + 0.063 | 99 |
| Present amide compound (compound No. 49) + Fludioxonil | 2.5 + 0.031 | 83 |
| Present amide compound (compound No. 49) + Fludioxonil | 0.63 + 0.063 | 99 |

Test Example 4

Each of the present amide compounds and fludioxonil was dissolved in dimethyl sulfoxide (DMSO) so as to obtain the concentration that is 150 times the test concentration, and a DMSO solution of each of the present amide compounds and a DMSO solution of fludioxonil were respectively dispensed into each well of a titer plate (with 96 wells) in the amount of 1 μl. Then, 148 μl of a suspension of a liquid complete medium containing conidia of gray mold (*Botrytis cinerea*) suspended in advance therein, so as to obtain the concentration of $1 \times 10^5$ conidia/ml, was added. The plate thus obtained was used as a plate in a treated area.

In contrast, 2 μl of DMSO was dispensed into each well of a titer plate (with 96 wells), and then 148 μl of a suspension of a liquid complete medium containing conidia of gray mold suspended in advance therein, so as to obtain the concentration of $1 \times 10^5$ conidia/ml, was added in the same manner as in the case of the treated area. The plate thus obtained was used as a plate in a non-treated area.

Each of the plate in a treated area and the plate in a non-treated area was cultured at 18° C. for 4 days, thereby allowing gray mold to undergo proliferation, and then the absorbance at 550 nm of each well of the titer plate was measured. The value obtained by subtracting the absorbance of the well, into which 150 μl of only a liquid complete medium has been dispensed, from this value was regarded as the degree of growth of gray mold. Based on the calculated degree of growth in a treated area and the calculated degree of growth in non-treated area, bactericidal effect was calculated using Equation 1.

TABLE 5

| Test compounds | Test concentration (ppm) | Bactericidal effect |
|---|---|---|
| Present amide compound (compound No. 11) + Fludioxonil | 1.3 + 0.013 | 96 |
| Present amide compound (compound No. 19) + Fludioxonil | 2.5 + 0.013 | 97 |
| Present amide compound (compound No. 31) + Fludioxonil | 1.3 + 0.013 | 98 |

TABLE 5-continued

| Test compounds | Test concentration (ppm) | Bactericidal effect |
|---|---|---|
| Present amide compound (compound No. 32) + Fludioxonil | 1.3 + 0.013 | 97 |
| Present amide compound (compound No. 43) + Fludioxonil | 1.3 + 0.013 | 98 |
| Present amide compound (compound No. 50) + Fludioxonil | 1.3 + 0.013 | 97 |

The invention claimed is:

1. A plant disease control composition comprising: an amide compound represented by formula (I):

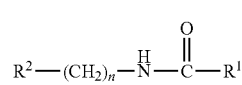

(I)

wherein n represents any integer of from 1 to 4, $R^1$ represents (hydroxycarbonyl)C1-C6 alkyl, (hydroxycarbonyl)C2-C6 alkenyl, (aminocarbonyl)C1-C6 alkyl, (aminocarbonyl)C2-C6 alkenyl, (C1-C6 alkoxy)carbonyl(C1-C6)alkyl, or (C1-C6 alkoxy)carbonyl(C2-C6) alkenyl, and $R^2$ represents phenyl, 1-naphthyl, or 3-indolyl, provided that, in the substituent represented by $R^2$, any carbon atom which composes phenyl, 1-naphthyl, and 3-indolyl, may each independently have halogen atom, hydroxyl, nitro, C1-C6 alkyl, or C1-C6 alkoxy as a substituent, and fludioxonil.

2. The plant disease control composition according to claim 1, wherein a ratio of the content of the amide compound to that of fludioxonil is from 1,000:1 to 1:10 in terms of a weight ratio.

3. A method for controlling plant diseases, which comprises the step of applying of an effective amount of the plant disease control composition according to claim 1 to plants or soil in which plants are grown.

4. A method for controlling plant diseases, which comprises the step of applying an effective amount of the plant disease control composition according to claim 1 to plant seeds.

5. The method for controlling plant diseases according to claim 4, wherein the plant seeds are seeds of corn, cotton, soybean, sugar beet, rapeseed, wheat, or rice.

6. A method for controlling plant diseases, which comprises the step of applying of an effective amount of the plant disease control composition according to claim 2 to plants or soil in which plants are grown.

7. A method for controlling plant diseases, which comprises the step of applying an effective amount of the plant disease control composition according to claim 2 to plant seeds.

* * * * *